(12) United States Patent
Keller

(10) Patent No.: US 7,553,333 B2
(45) Date of Patent: Jun. 30, 2009

(54) HIP PROSTHESIS PROVIDED WITH A SHAFT INSERTED INTO THE FEMUR

(75) Inventor: Arnold Keller, Kayhude (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 10/558,405

(22) PCT Filed: Jun. 16, 2004

(86) PCT No.: PCT/EP2004/006485

§ 371 (c)(1),
(2), (4) Date: Nov. 28, 2005

(87) PCT Pub. No.: WO2005/007039

PCT Pub. Date: Jan. 27, 2005

(65) Prior Publication Data

US 2007/0010891 A1    Jan. 11, 2007

(30) Foreign Application Priority Data

Jul. 16, 2003 (EP) .................... 03016157

(51) Int. Cl.
*A61F 2/36* (2006.01)
(52) U.S. Cl. ........................... 623/23.14
(58) Field of Classification Search ... 623/19.11–20.13, 623/22.11–23.39
See application file for complete search history.

(56) References Cited

U.S. PATENT DOCUMENTS

| | | | | |
|---|---|---|---|---|
| 4,141,088 A | * | 2/1979 | Treace et al. | 623/22.41 |
| 4,261,063 A | * | 4/1981 | Blanquaert | 623/23.46 |
| 4,279,042 A | * | 7/1981 | Andriacchi et al. | 623/23.15 |
| 4,495,664 A | * | 1/1985 | Blanquaert | 623/23.36 |
| 4,530,116 A | * | 7/1985 | Frey | 623/23.29 |
| 4,549,319 A | * | 10/1985 | Meyer | 623/23.23 |
| 4,623,349 A | * | 11/1986 | Lord | 623/23.44 |
| 4,731,088 A | * | 3/1988 | Collier | 623/22.13 |
| 4,784,124 A | * | 11/1988 | Kaltenbrunner et al. | 606/63 |
| 5,002,580 A | * | 3/1991 | Noble et al. | 623/23.23 |
| 5,108,453 A | * | 4/1992 | Kotz et al. | 623/23.29 |

(Continued)

FOREIGN PATENT DOCUMENTS

DE    29522382 U    9/2002

(Continued)

OTHER PUBLICATIONS

International Search Report mailed Sep. 20, 2004, issued in counterpart application PCT/EP2004/006485.

*Primary Examiner*—David J. Isabella
*Assistant Examiner*—Ann Schillinger
(74) *Attorney, Agent, or Firm*—Morrison & Foerster LLP

(57) ABSTRACT

A hip prosthesis includes a shaft which can be inserted into a hole in the femur without using cement. The proximal section of the shaft includes a base body having a form that is complementary to the shape of the hole in the femur into which the shaft is to be inserted. The hole is made using a tool of a shape corresponding to the base body. The base body has a cuneus rib raised on its dorsal or ventral surface that has a width in its center that is at least three times its height. The rear surface of the cuneus rib has rough and abrasive properties.

9 Claims, 1 Drawing Sheet

U.S. PATENT DOCUMENTS

| | | | |
|---|---|---|---|
| 5,290,311 A | | 3/1994 | Baumann |
| 5,480,452 A | * | 1/1996 | Hofmann et al. .......... 623/23.28 |
| 5,593,446 A | * | 1/1997 | Kuoni ..................... 623/23.44 |
| 5,607,607 A | * | 3/1997 | Naiman et al. .......... 219/121.68 |
| 5,645,740 A | * | 7/1997 | Naiman et al. .......... 219/121.68 |
| 5,728,161 A | | 3/1998 | Camino |
| 5,755,799 A | * | 5/1998 | Oehy et al. .............. 623/18.11 |
| 5,755,811 A | * | 5/1998 | Tanamal et al. .......... 623/23.35 |
| 5,888,210 A | * | 3/1999 | Draenert .................. 623/23.35 |
| 5,935,172 A | * | 8/1999 | Ochoa et al. ............. 623/23.36 |
| 6,030,417 A | * | 2/2000 | Bresler et al. ............ 623/23.15 |
| 6,083,522 A | * | 7/2000 | Chu et al. ................... 424/423 |
| 6,168,632 B1 | | 1/2001 | Moser |
| 6,190,416 B1 | * | 2/2001 | Choteau et al. .......... 623/22.12 |
| 6,702,854 B1 | * | 3/2004 | Cheal et al. .............. 623/22.42 |
| 6,770,100 B2 | * | 8/2004 | Draenert .................. 623/23.26 |
| 7,044,975 B2 | * | 5/2006 | Cheal et al. .............. 623/22.42 |
| 2002/0045950 A1 | * | 4/2002 | Draenert .................. 623/23.26 |
| 2004/0010319 A1 | * | 1/2004 | McTighe et al. .......... 623/23.21 |
| 2004/0107001 A1 | * | 6/2004 | Cheal et al. .............. 623/22.42 |
| 2004/0236430 A1 | * | 11/2004 | Koch et al. ................ 623/23.31 |

FOREIGN PATENT DOCUMENTS

| | | |
|---|---|---|
| EP | 0159462 B1 | 5/1988 |
| EP | 0567349 A | 10/1993 |
| EP | 0780106 A | 6/1997 |
| EP | 0761183 B1 | 5/2002 |
| EP | 1070490 B1 | 10/2003 |
| FR | 2633509 A | 1/1990 |
| WO | WO-93/08770 A | 5/1993 |

* cited by examiner

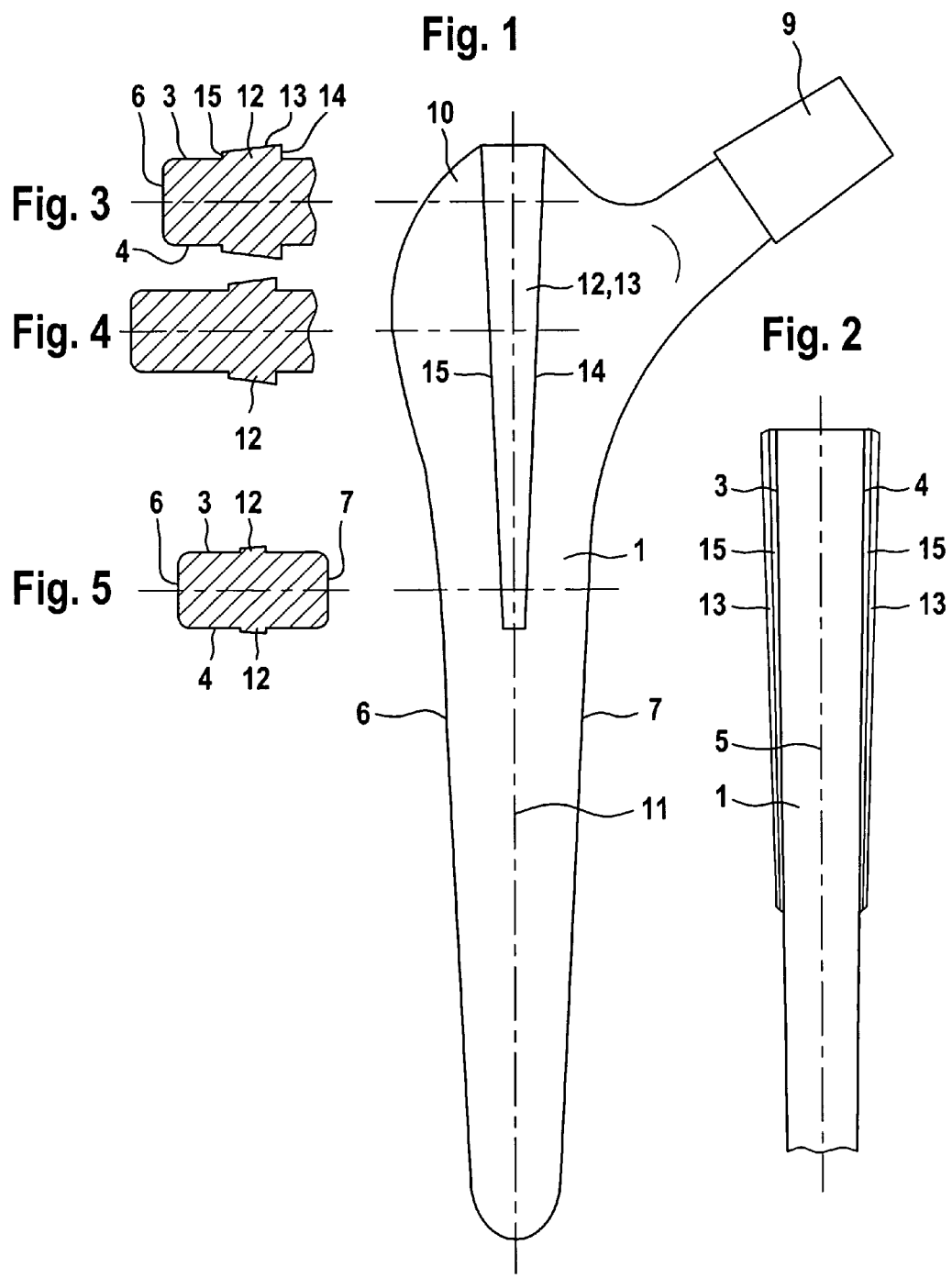

HIP PROSTHESIS PROVIDED WITH A SHAFT INSERTED INTO THE FEMUR

FIELD AND BACKGROUND OF THE INVENTION

The part of a hip prosthesis assigned to the femur is equipped with a shaft inserted into a cavity which, after resection of the head and neck of the hip, is formed by a suitable tool in the spongy inner cross-sectional area of the femur. If the shaft is inserted without using cement, it is endeavored to make the shape of the cavity as far as possible complementary to the shape of the shaft, so that the prosthesis has a secure and firm fit after insertion of the shaft. The proximal portion of the shaft coming to lie in the metaphyseal region of the bone (approximately above the lesser trochanter) is designed in such a way that it can transmit not only vertical forces in the direction of the femur but also forces extending transverse thereto and, in particular, medially directed forces. To ensure that the surface areas of the proximal prosthesis shaft oriented in the ventral and dorsal directions also take part in transmission of forces to the bone, it is known to design their surface such that a form-fit connection with the bone tissue can be obtained. Two possibilities are available for this, namely, on the one hand, a surface micro-roughness which is brought about, for example, by glass blasting, porous coating or the like, and allows the bone to infiltrate into the depressions and pores, and, on the other hand, ribs which project from the base body of the shaft. These two possibilities can also be used together. Thus, it is known (EP-B-761 183; U.S. Pat. No. 5,755,811) to arrange ribs on the dorsal and ventral faces of the proximal base body of the shaft, said ribs extending in the longitudinal direction of the shaft, and their cross section increasing in a wedge shape from distal to proximal. Such ribs are referred to below as wedge-shaped ribs. The cavity is produced using a rasp whose shape corresponds to the base body of the shaft without the ribs. Upon insertion of the shaft, the base body of the shaft forms a press fit with the surface of the cavity. The wedge-shaped ribs cut into the spongy bone tissue as the prosthesis is being inserted. Because of their wedge shape, they displace and compact the bone tissue. This contributes to the secure fit of the prosthesis. First, a macroscopic form fit is thus obtained between the bone and the prosthesis cross section, by virtue of the rib. Second, a microscopic form fit is obtained after bone tissue has grown into the rough or porous surface structure. These two effects evidently occur independently of one another and are used independently of one another in the construction of a prosthesis.

Of course, the said compression of the bone material during insertion of a wedge-shaped rib must not lead to the bone breaking. This danger is all the greater, the wider a rib, because the latter then directs a greater wedge surface toward the cortical bone and produces a greater wedging force against the cortical bone. Known wedge-shaped ribs are therefore made of a narrow design (EP-B-761 183, EP-B-159 462). For the same reason, it is sought to deflect the wedging action of the ribs into the tangential direction (DE-U-295 22 382, page 4, line 22). It is true that wide ribs are also known in hip prostheses intended for cementless implantation (EP-A-10 70 490; EP-A-567349). However, these are ribs which, because of their shape, are unsuitable for displacement and compression of bone material and therefore require a shaping of the cavity such that their volume and their shape are taken into consideration from the outset in the cavity. Relatively wide shaft projections broadening from distal to proximal are also known for prosthesis shafts which are intended to be implanted using cement and in which, therefore, the associated tool is designed such that the artificial bone cavity is more voluminous than the shaft inclusive of its rib-like attachments.

SUMMARY OF THE INVENTION

The object of the invention is to make available a prosthesis shaft for cementless implantation with wedge-shaped ribs making up a rib assembly and a rough surface, said prosthesis shaft permitting rapid and extensive adherence between the prosthesis surface and the bone tissue. The solution according to the invention lies in the features of as disclosed herein, that the wedge-shaped rib assembly is on average at least three times as wide as it is high and the roughness on its rear face is sharp-edged with a peak-to-valley height of between 0.05 and 0.5 mm.

Based on previous experience, one has to expect that a wide wedge-shaped rib of this kind will deploy its wedging effect mainly outwardly toward the cortical bone and that, therefore, there will be a danger of the bone breaking. This danger would in fact arise if the rear face of the rib were not rough. The roughness means that the bone substance which comes into direct contact with the rear face of the rib, and which is exposed to the wedging effect and relative movement, is abraded and crushed and thus brought into a flow-able state so that it can be displaced to the sides away from the rear face of the rib and can flow off. This has two consequences. First, the force generated in the direction perpendicular to the rear face of the rib is comparatively small, as a result of which the possibly damaging effect of the force on the cortical bone is limited. Second, the rear face of the rib, in the final state of implantation, is situated in immediate proximity to undamaged bone substance in which the natural vascular system is preserved, since the previously crushed bone substance has been removed by virtue of its flowability. This means that the process of infiltration of new bone substance reaches the porous rear face of the rib very quickly after implantation and that, as a result, an intimate and extensive surface union is created after just a short time. It may well be that such an effect also occurred in the previously known wedge-shaped ribs with rough surface at their cross-sectional tip. However, since this effect was limited to a very small surface area, it was not appreciable and it also made no positive contribution. At the rib flanks, the situation is fundamentally different. In the case of individual ribs, a comparatively wide compression space is present in the compression direction perpendicular to the flank surface, so that although the bone substance is compressed and partially squeezed, the pressing is not as great as would be required for an appreciable abrasive effect of the roughness. The bone substance remains more or less in situ. Since the vessels therein are for the most part destroyed, it initially forms a barrier between the undamaged bone tissue and the prosthesis surface through which, after implantation, fresh bone tissue must first have penetrated before it can infiltrate the rough surface of the prosthesis and bring about a form-fit connection. In the interstices between adjacent ribs, the situation is once again different than at the rear of the rib, because there the compression and tissue destruction is particularly pronounced, without the destroyed tissue being able to be removed. In this area too, the connection to fresh bone tissue can therefore take place only with some delay.

The invention thus affords the advantage that, by virtue of the roughness of the large rear face of the rib, and because of the resulting closeness of undamaged bone tissue, a firm connection between prosthesis surface and bone surface can take place very quickly.

In the whole of the proximal portion, the rib is preferably at least three times as wide, preferably four times as wide, as it is high. To ensure that the abrasive action of the roughness during the relative movement of the rib surface with respect to the pressed-on bone tissue is at all times sufficient compared to the squeezing generated by the wedging effect, the wedge angle, that is to say the angle between the surface of the rear of the rib and the midplane extending in the lateral-medial direction (LM midplane) of the shaft, must not be greater than 5°, preferably not greater than 3.5°, and more preferably not greater than 2.5°.

The width of the rib too, that is to say its dimension in the LM direction, preferably increases from distal to proximal, and the angle between the lateral edge and the longitudinal direction of the shaft must not be greater than 4°, preferably 3°. The same applies to the lateral edge.

In the shaft cross section, the rear face of the rib must extend approximately parallel to the LM midplane. The angle between the rear face of the rib and the LM midplane is preferably not greater than 15°, the rib height increasing toward the lateral face. The medial flank expediently extends from the rear face of the rib to form a sharp edge and runs substantially perpendicular to the LM plane. The same expediently applies to the lateral edge too, although it is less important there.

To ensure that the abrasive effect of the roughness is sufficient in the area of the rear of the rib, the distance between adjacent peaks of the roughness is expediently of the same order of magnitude as the peak-to-valley height, namely between 0.05 and 0.5 mm.

BRIEF DESCRIPTION OF THE DRAWINGS

The invention is explained in more detail below with reference to the drawing which depicts an advantageous illustrative embodiment and in which:

FIG. 1 shows a side view,

FIG. 2 shows a view from the lateral direction, and

FIGS. 3-5 show cross sections through the prosthesis shaft at respectively corresponding heights thereof.

DETAILED DESCRIPTION OF THE INVENTION

The prosthesis is a straight shaft prosthesis, that is to say the shaft has a continuously straight longitudinal axis and is implanted in a rectilinear direction into the femur. The shaft 1 comprises an in cross section substantially rectangular base body with parallel dorsal and ventral faces 3, 4 which taper in a wedge shape in the distal direction. They each enclose an angle of less than 2° with the lateral-medial midplane 5. The lateral and medial boundary faces 6, 7 of the base body of the shaft likewise taper in a wedge shape in the distal direction. The proximal end is adjoined by the prosthesis neck, having a cone 9 for attachment of a ball joint, and by a lateral wing 10 in the region of the greater trochanter.

A rasp (not shown) for forming the bone cavity intended to receive the prosthesis shaft has the same shape as the base body of the prosthesis shaft delimited by the faces 3, 4 and 6, 7, as is generally known, in order to give the prosthesis shaft a secure and firm fit in the bone cavity after implantation.

On the dorsal and ventral faces 3, 4 of the base body of the shaft, and approximately centrally with respect to the shaft axis 11, ribs 12 are attached which have the shape of a wedge with straight boundary faces. The size of these faces is the dorsally or ventrally oriented rear face 13. Medially, the rib is delimited by a medial end face extending approximately perpendicular to the surface 3 or 4. The same applies to the lateral end face 15.

With the center line 11, the end faces 14, 15 enclose, like the boundary edges of the rear face 13, an angle of in each case approximately 2.5°. The angle which the rear faces 13 of the rib enclose with the LM mid-plane of the shaft is 2°.

The rear face 13 of the rib extends approximately parallel to the LM midplane 5 of the shaft. In the example shown, the deviation amounts to less than 10°. At the medial edge, the rib is slightly higher than at the lateral edge, thereby increasing the macroscopic form-fit for transmitting force from the prosthesis medially to the bone.

At least the rear face 13 of the rib 12 is provided with a rough and, if appropriate, porous surface by means of sandblasting, plasma coating, flame spraying or the like. The roughness elevations are sharp-edged so that, when the shaft is pushed into the bone, they act abrasively on the bone substance. Such a roughness can also be provided on the other faces of the prosthesis shaft in order to permit intimate connection of the bone tissue with the prosthesis surface. As far as the invention is concerned, what matters is simply the roughness of the rear face 13 of the rib. Whereas the base body of the shaft has been provided with a complementary shape in the bone cavity and acquires the desired press fit therein without any appreciable additional deformation of the bone, there is no such complementary cavity form for the ribs 12. When the shaft is introduced into the bone, the ribs displace an amount of the bone tissue corresponding to their volume. If the rear face were smooth, the laminar structure of the bone would simply be compressed and compacted, in which case the liquid content of the lamellar interstices would escape. Thanks to the abrasive quality of the back of the rib, the bone lamellas in the case of the invention are abraded and cut. In this way, they can escape with the liquid interstitial content from the area between the rear face of the rib and the solid and undamaged bone tissues lying behind them. On the one hand, this reduces the pressing that arises because of the wedge effect of the ribs between these and the bone. On the other hand, the spongy bone substance located between the rear face of the rib and the hard cortical bone is not totally compressed and damaged. Instead, it remains intact, almost as far as the rib surface, and can therefore contribute to rapid securing of the prosthesis by means of fresh bone tissue rapidly advancing to the shaft surface and infiltrating the surface roughness thereof.

The invention claimed is:

1. A hip prosthesis set comprising: a hip prosthesis having a shaft which is configured to be inserted into a femoral cavity without using cement, a proximal portion of the shaft comprising a base body, a first rib projecting dorsally from the base body relative to an implanted position and a second rib projecting ventrally from the base body relative to the implanted position, each of the ribs having two flanks and a rear face and extending parallel to the shaft direction, increasing in height from a distal portion of the shaft to the proximal portion for displacing and compressing spongy bone tissue as the prosthesis is inserted into the femoral cavity and having a rough surface to encourage bone ingrowth, and a tool which is configured to shape the cavity so that it substantially corresponds to the shape of the base body, wherein each of the ribs is on average at least three times as wide as it is high and the rough surface has a roughness on its rear face that is sharp-edged with a peak-to-valley height range of between 0.05 and 0.5 mm.

2. The hip prosthesis set as claimed in claim 1, wherein the hip prosthesis is a straight shaft prosthesis.

3. The hip prosthesis set as claimed in claim 1 or 2, wherein the rear face of each of the ribs extends, in a shaft cross section, approximately parallel to a lateral-medial midplane of the shaft relative to the implanted position.

4. The hip prosthesis set as claimed in claim 3, wherein the height of each of the ribs, at an edge delimiting it medially, is greater than at its lateral boundary.

5. The hip prosthesis set as claimed in claim 4, wherein a medial end face of each of the ribs extends approximately perpendicular to the surface of the base body of the shaft.

6. The hip prosthesis set as claimed in claim 3, wherein a medial end face of each of the ribs extends approximately perpendicular to the surface of the base body of the shaft.

7. The hip prosthesis set as claimed in claim 1 or 2, wherein a medial end face of each of the ribs extends approximately perpendicular to the surface of the base body of the shaft.

8. The hip prosthesis set as claimed in claim 1, wherein the distance between the peaks of the elevations forming the roughness on the rear face of each of the ribs is of the same order of magnitude as the peak-to-valley height.

9. The hip prosthesis set as claimed in claim 1, wherein only a single first rib and a single second rib project from the base body.

\* \* \* \* \*

UNITED STATES PATENT AND TRADEMARK OFFICE
CERTIFICATE OF CORRECTION

PATENT NO. : 7,553,333 B2
APPLICATION NO. : 10/558405
DATED : June 30, 2009
INVENTOR(S) : Arnold Keller It is certified that error appears in the above-identified patent and that said Letters Patent is hereby corrected as shown below:

On the Title Page

Item (30), "Foreign Application Priority Data," please replace "03016157" with --03016157.4--.

Signed and Sealed this

Twenty-ninth Day of September, 2009

David J. Kappos
*Director of the United States Patent and Trademark Office*